(12) United States Patent
Welsh et al.

(10) Patent No.: US 6,635,432 B1
(45) Date of Patent: Oct. 21, 2003

(54) PEPTIDE POTENTIATION OF ACID-SENSORY ION CHANNEL IN PAIN

(75) Inventors: Michael J. Welsh, Riverside, IA (US); Candice C. Askwith, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/557,506

(22) Filed: Apr. 25, 2000

(51) Int. Cl.$^7$ .................. G01N 33/566; C12P 21/06; C12N 1/20; C07H 21/04; C07K 1/00
(52) U.S. Cl. .................. 435/7.21; 435/6; 435/4; 435/69.1; 435/252.3; 435/320.1; 530/300; 530/350; 536/23.5; 436/501
(58) Field of Search .................. 435/4, 7.21, 6, 435/69.1, 252.3, 320.1; 436/501; 530/300, 350; 536/23.5

(56) References Cited

U.S. PATENT DOCUMENTS 5,892,018 A    4/1999   Welsh et al.

FOREIGN PATENT DOCUMENTS

| WO | WO 98/35034 | 8/1998 |
|----|-------------|--------|
| WO | WO 00/08149 | 2/2000 |

OTHER PUBLICATIONS

Catarsi, S. et al., Neuropharmacology 41(592–600)2001.*
Askwith et al., Neuron, 26(1)133–41, Apr. 2000.*
Perry et al. J. Neuroscience, 21(15)5559–5567, 2001.*
O'Gara, Bruce A. et al., "Regulation of pharyngeal motility by FMRFamide and related peptides in the medical leech, Hirudo medicinalis", Invertebrate Neuroscience, 1999, 4: 41–53.
Sakai H. et al., Cloning and functional expression of a novel degenerin–like Na+ channel gene in mammals, Journal of Physiology, 1999, 519.2: 323–333.
Lopes, C M B et al., "Actions of general anaesthetics and arachidonic acid pathway inhibitors on K+ currents activated by volatile anaesthetics and FMRFamide in molluscan neurones.", British Journal of Pharmacology, 1998, 125.2: 309–318.
Askwith, C C et al., "FMRFamide–related peptides potentiate acid–evoked currents from sensory neurons and DEG/ENaC channels.", Society for Neuroscience Abstracts, 2000, No. 18.4.
Waldmann, R., et al., The J. of Biological Chem. 271(18):10433–10436, "The Mammalian Degenerin MDEG, an Amiloride–sensitive Cation Channel Activated by Mutations Causing Neurodegeneration in *Caenorhabditis elegans*" (1996).
Price, M., et al., The J. of Biological Chem. 271(14):7879–7882, "Cloning and Expression of a Novel Human Brain Na+ Channel" (1996).
Kriegler, M., in Gene Transfer and Expression: A Laboratory Manual, pp. 3–176. Stockton Press, NY, NY 1990.

* cited by examiner

*Primary Examiner*—Yvonne Eyler
*Assistant Examiner*—Michael T Brannock
(74) *Attorney, Agent, or Firm*—McKee, Voorhees & Sease, P.L.C.

(57) ABSTRACT

An assay for determining agonists, antagonists, or modulators for acid-sensing ion channels. The assay is especially useful for screening analgesics. The screening assay can be provided in a kit form. The assay comprises administering the composition to be screened to cells expressing acid-gated channels and then determining whether the composition inhibits, enhances, or has no effect on the channels when acid is introduced. The determination can be performed by analyzing whether a current is sustained by the cells in the presence of the composition and the acid. This current can be compared to that sustained by the FMRFamide and related peptides.

11 Claims, 9 Drawing Sheets

SEQUENCE LISTING

<160> NUMBER OF SEQ ID NOS: 5

<210> SEQ ID NO 1
<211> LENGTH: 4
<212> TYPE: PRT
<213> ORGANISM: Caenorhabditis elegans

<400> SEQUENCE: 1

Phe Met Arg Phe
1

<210> SEQ ID NO 2

```
<211> LENGTH: 7
<212> TYPE: PRT
<213> ORGANISM: Caenorhabditis elegans

<400> SEQUENCE: 2

Thr Gly Gly Thr Met Arg Phe
1               5

<210> SEQ ID NO 3
<211> LENGTH: 8
<212> TYPE: PRT
<213> ORGANISM: Rattus norvegicus

<400> SEQUENCE: 3

Phe Leu Phe Gln Pro Gln Arg Phe
1               5

<210> SEQ ID NO 4
<211> LENGTH: 6
<212> TYPE: PRT
<213> ORGANISM: Rattus norvegicus

<400> SEQUENCE: 4

Phe Leu Phe Gln Arg Phe
1               5

<210> SEQ ID NO 5
<211> LENGTH: 8
<212> TYPE: PRT
<213> ORGANISM: Rattus norvegicus

<400> SEQUENCE: 5

Phe Leu Phe Gln Pro Gln Arg Phe
1               5
```

PEPTIDE POTENTIATION OF ACID-SENSORY ION CHANNEL IN PAIN

BACKGROUND OF THE INVENTION

FMRFamide (Phe-Met-Arg-Phe amide) and related peptides comprise a family of neuropeptides that are abundant in many invertebrates, including *Caenorhabditis elegans* (Nelson, L. S., Kim, K., Memmott, J. E., and Li, C. (1998). FMRFamide-related gene family in the nematode, *Caenorhabditis elegans*. Mol Brain Res 58, 103–111), *Aplysia californica* (Greenberg, M. J., and Price, D. A. (1992). Relationships among the FMRFamide-like peptides. Prog Brain Res. 92, 25–37), and *Drosophila melanogaster* (Schneider, L. E., and Taghert, P. H. (1988). Isolation and characterization of a Drosophila gene that encodes multiple neuropeptides related to Phe-Met-Arg-Phe-NH2 (FMRF amide). Proc Natl Acad Sci USA 85, 1993–1997). In these organisms, FMRFamide-like neuropeptides act as neurotransmitters and neuromodulators. At least one gene encoding FMRFamide-related peptides is present in mammals; it produces neuropeptide FF and neuropeptide AF (A18Famide) (Perry, S. J., Huang, E. Y. K., Cronk, D., Bagust, J., Sharma, R., Walker, R. J., Wilson, S., and Burke, J. F. (1997). A human gene encoding morphine modulation peptides related to NPFF and FMRF amide, FEBS Lett 409, 426–430; Vilim, F. S., Aarnisalo, A. A., Nieminen, M. L., Lintunen, M., Karlstedt, K., Kontinen, V. K., Kalso, E., States, B., Panula, P., and Ziff, E. (1999). Gene for pain modulatory neuropeptide NPFF: induction in spinal cord by noxious stimuli. Mol Pharmacol 55, 804–811). Although FMRFamide itself has not been discovered in mammals (Yang, H. Y. T., Fratta, W., Majane, E. A., and Costa, E. (1985). Isolation, sequencing, synthesis, and pharmacological characterization of two brain neuropeptides that modulate the action of morphine. Proc Natl Acad Sci USA 82, 7757–7761), administration of FMRFamide induces a variety of physiologic effects, including alterations in blood pressure, respiratory rate, glucose-stimulated insulin release, and behavior (Kavaliers, G. M., and Hirst, M. (1985). FMRFamide, a putative endogenous opiate antagonist: evidence from suppression of defeat-induced analgesia and feeding in mice. Neuropeptides 6, 485–494; Kavaliers, M. (1987). Calcium channel blockers inhibit the antagonistic effects of Phe-Met-Arg-Phe-amide (FMRFamide) on morphine- and stress-induced analgesia in mice. Brain Res 415, 380–384; Mues, G., Fuchs, I., Wei, E. T., Weber, E., Evans, C. J., Barchas, J. D., and Chang, J.-K. (1982). Blood pressure elevation in rats by peripheral administration of Tyr-Gly-Gly-Phe-Met-Arg-Phe and the invertebrate neuropeptide, Phe-Met-Arg-Phe-NH2. Life Sciences 31, 2555–2561; Muthal, A. V., Mandhane, S. N., and Chopde, C. T. (1997). Central administration of FMRFamide produces antipsychotic-like effects in rodents. Neuropeptides 31, 319–322; Nishimura, M., Ohtsuka, K., Takahashi, H., and Yoshimura, M. (2000). Role of FMRFamide-Activated Brain Sodium Channel in Salt-Sensitive Hypertension. Hypertension 35, 443–450; Raffa, R. B., Heyman, J., and Porreca, F. (1986) Intrathecal FMRFamide (Phe-Met-Arg-Phe-NH2) induces excessive grooming behavior in mice. Neuroscience Lett 65, 94–98; Sorenson, R. L., Sasek, C. A., and Elde, R. P. (1984). Phe-Met-Arg-Phe-amide (FMRF-NH2) inhibits insulin and somatostatin secretion and anti-FMRF-NH2 sera detects pancreatic polypeptide cells in the rat islet. Peptides 5, 777–782; Tekegdy, G., and Bollók, I. (1987). Amnesic action of FMRFamide in rats. Neuropeptides 10, 157–163; Thiemermann, C., Al-Damluji, S., Hecker, M., and Vane, J. R. (1991). FMRF-amide and L-Arg-1-Phe increase blood pressure and heart rate in the anaesthetized rate by central stimulation of the sympathetic nervous system. Biochem Biophys Res Comm 175, 318–324). In mammals, FMRFamide and neuropeptide FF also modify the response to painful stimuli and are induced by inflammation (Kontinen, V. K., Aarnisalo, A. A., Idanpaan-Heikkila, J. J., Panula, P., and Kalso, E. (1997). Neuropeptide FF in the rat spinal cord during carrageenan inflammation. Peptides 18, 287–292; Raffa, R. B., and Connelly, C. D. (1992). Supraspinal antinociception produced by [D-Met2]-FMRFamide in mice. Neuropeptides 22, 195–203; Tang, J., Yang, H. Y. T., and Costa, E. (1984). Inhibition of spontaneous and opiate-modified nociception by an endogenous neuropeptide with Phe-Met-Arg-Phe-NH2-like immunoreactivity. Proc Natl Acad Sci USA 81, 5002–5005; Vilim, F. S., Aarnisalo, A. A., Nieminen, M. L., Lintunen, M., Karlstedt, K., Kontinen, V. K., Kalso, E., States, B., Panula, P., and Ziff, E. (1999). Gene for pain modulatory neuropeptide NPFF: induction in spinal cord by noxious stimuli. Mol Pharmacol 55, 804–811; Yang, et al. (1985)). When FMRFamide and related peptides are injected intracerebroventricularly, they elicit hyperalgesia and a reduction in morphine-induced analgesia (Brussard, A. B., Kits, K. S., Ter Maat, A., Mulder, A. H., and Schoffelmeer, A. N. M. (1989). Peripheral injection of DNA-RFa, a FMRFa agonist, suppresses morphine-induced analgesia in rats. Peptides 10, 735–739; Kavaliers (1987); Raffa, R. B. (1988). The action of FMRFamide (Phe-Met-Arg-Phe-NH2) and related peptides on mammals. Peptides 9, 915–922; Roumy, M., and Zajac, J. M. (1998). Neuropeptide FF, pain and analgesia. Euro J. Pharm 345, 1–11; Tang et al. (1984); Yang, et al. (1985)). In addition, FMRFamide immunoreactive material is released in mammals following chronic morphine administration, and anti-FMRFamide antibodies can enhance morphine's effects (Devillers, J. P., Boisserie, F., Laulin, J. P., Larcher, A., and Simonnet, G. (1995). Simultaneous activation of spinal antiopioid system (neuropeptide FF) and pain facilitatory circuitry by stimulation of opioid receptors in rats. Brain Research 700, 173–181; Tang, et al. (1984)).

Some effects of FMRFamide and neuropeptide FF appear to be mediated through opioid receptors; these effects are blocked by the opioid antagonist naloxone (Gouardéres, C., Sutak, M., Zajak, J. M. and Jhamandas, K. (1993). Antinociceptive effects of intrathecally administered F8Famide and FMRFamide in the rat. Eur J Pharm 237, 73–81; Kavaliers and Hirst (1985); Kavaliers (1987); Raffa (1988); Roumy and Zajac (1998)). Yet other effects of FMRFamide and FMRFamide-related peptides are independent of opioid receptors and are insensitive to naloxone (Allard, M., Geoffre, S., Legendre, P., Vincent, J. D., and Simonnet, G. (1989). Characterization of rat spinal cord receptors to FLFQPQRFamide, a mammalian morphine modulating peptide: a binding study. Brain Research 500, 169–176; Gayton, R. J. (1982). Mammalian neuronal actions of FMRFamide and the structurally related opioid Met-enkephalin-Arg6-Phe7. Nature 298, 275–176; Kavaliers (1987); Raffa (1988); Raffa, et al. (1986); Roumy and Zajac (1998)). In mammals, the non-opioid receptor(s) for FMRFamide and related peptides have not been identified, and it is not known how these peptides modulate pain sensation. However, the discovery of a FMRFamide-activated $Na^+$ channel (FaNaCh) in the mollusc *Heix aspersa* (Lingueglia, E., Champigny, G., Lazdunski, M., and Barbry, P. (1995). Cloning of the amiloride-sensitive FMRFamide peptide-gated sodium channel. Nature 378, 730–733) provided a clue that similar receptors might exist in mammals.

Unlike many neuropeptide receptors, FaNaCh is an ion channel gated directly by its peptide ligand, FMRFamide (Lingueglia, et al. (1995)). The neuropeptide receptor, FaNaCh, is a member of the DEG/ENaC family of channels. DEG/ENaC channels are homo- or hetero-multimers composed of multiple subunits (Bassilana, F., Champigny, G., Waldmann, R., de Weille, J. R., Heurteaux, C., and Lazdunski, M. (1997). The acid-sensitive ionic channel subunit ASIC and the mammalian degenerin MDEG form a heteromultimeric $H^+$-gated $Na^+$ channel with novel properties. J. Biol Chem 272, 28819–28822; Coscoy, S., Lingueglia, E., Lazdunski, M., and Barbry, P. (1998). The Phe-Met-Arg-Phe-amide-activated sodium channel is a tetrameter. J Biol Chem 273, 8317–8322; Lingueglia, E., de Weille, J. R., Bassilana, F., Heurteaux, C., Sakai, H., Waldmann, R., and Lazdunski, M. (1997). A modulatory subunit of acid sensing ion channels in brain and dorsal root ganglion cells. J Biol Chem 272, 29778–29783; Waldmann, R., and Lazdunski, M. (1998). $H^+$-gated cation channels: neuronal acid sensors in the NaC/DEG family of ion channels. Curr Opin Neurobiol 8, 418–424). Each subunit contains two transmembrane domains separated by a large extracellular cysteine-rich domain, and cytosolic N- and C-termini (Waldmann and Lazdunski (1998)). DEG/ENaC channels are not voltage-gated and are cation-selective (usually $Na^+>K^+$). FaNaCh is the only known DEG/ENaC channel which acts as a neuropeptide receptor. Other members of this family are involved in mechanosensation, salt taste, and epithelial $Na^{30}$ absorption (Lindemann, B. (1996). Taste reception. Physiol Rev 76, 718–766; Mano, I., and Driscoll, M. (1999). DEG/ENaC channels: a touchy superfamily that watches its salt. Bioessays 21, 568–578; Schild, L., Canessa, C. M., Shimkets, R. A., Gautschi, I., Lifton, R. P., and Rossier, B. C. (1995). A mutation in the epithelial sodium channel causing Liddle disease increases channel activity in the Xenopus laevis oocyte expression system. Proc Natl Acad Sci USA 92, 5699–5703; Snyder, P. M., Price, M. P., McDonald, F. J., Adams, C. M., Volk, K. A., Zeiher, B. G., Stokes, J. B., and Welsh, M. J. (1995). Mechanism by which Liddle's syndrome mutations increase activity of a human epithelial $Na^+$ channel. Cell 83, 969–978). Although a mammalian FaNaCh has not yet been isolated, mammals do possess multiple DEG/ENaC family members. Interestingly, one subset of this channel family, the acid-sensing ion channels, has been postulated to play a role in sensory perception and may, like FMRFamide, play a role in pain perception (Waldmann and Lazdunski (1998)). The acid-sensing DEG/ENaC channels respond to protons and generate a voltage-insensitive cation current when the extracellular solution is acidified.

The tissue acidosis associated with inflammation, infection, and ischemia causes pain (Reeh, P. W., and Steen, K. H. (1996). Tissue acidosis in nociception and pain. Prog Brain Res 113, 143–151). Acidosis also generates proton-dependent transient and sustained $Na^{30}$ currents in cultured sensory neurons (Bevan, S., and Yeats, J. (1991). Protons activate a cation conductance in a sub-population of rat dorsal root ganglion neurones. J Physiol (Lond) 433, 145–161; Davies, N. W., Lux, H. D., and Morad, M. (1988). Site and mechanism of activation of proton-induced sodium current in chick dorsal root ganglion neurones. J Physiol (Lond) 400, 159–187). Although the molecular identity of the channels responsible for these currents is unknown, they have been hypothesized to be acid-sensing members of the DEG/ENaC protein family based on their ion selectivity, voltage insensitivity, and expression pattern (Babinski, K., Le, K. T., and Séguéla, P. (1999). Molecular cloning and regional distribution of a human proton receptor subunit with biphasic Adfunctional properties. J. Neurochem 72, 51–57; Bassilana, et al. (1997); de Weille, J. R., Bassilana, F., Lazdunski, M., and Waldmann, R. (1998). Identification, functional expression and chromosomal localisation of a sustained human proton-gated cation channel. FEBS Lett 433,257–260; Lingueglia, et al. (1997); Waldmann, R., Bassilana, F., de Weille, J., Champigny, G., Heurteaux, C., and Lazdunski, M. (1997). Molecular cloning of a non-inactivating proton-gated $Na^+$ channel specific for sensory neurons. J Biol Chem 272, 20975–20978). The acid-sensing ion channels include the brain $Na^+$ channel 1 (BNC1) and its differentially spliced isoform MDEG2 (García-Anoveros, J., Derfler, B., Neville-Golden, J., Hyman, B. T., and Corey, D. P. (1997). BNaC1 and BNaC2 constitute a new family of human neuronal sodium channels related to degenerins and epithelial sodium channels. Proc Natl Acad Sci USA 94, 1459–1464; Lingueglia, et al. (1997); Price, M. P., Snyder, P. M., and Welsh, M. J. (1996). Cloning and expression of a novel human brain $Na^+$ channel. J Biol Chem 271, 7879–7882; Waldmann, R., Champigny, G., Voilley, N., Lauritzen, I., and Lazdunski, M. (1996). The mammalian degenerin MDEG, an amiloride-sensitive cation channel activated by mutations causing neurodegeneration in Caenorhabditis elegans. J Biol Chem 271, 10433–10436), the acid-sensing ion channel (ASICα) and its differentially spliced isoform ASICβ (Chen, C.-C., England, S., Akopian, A. N., and Wood, J. N. (1998). A sensory neuron-specific, proton-gated ion channel. Proc Natl Acad Sci USA 95, 10240–10245; Waldmann, et al. (1997)), and the dorsal root acid-sensing ion channel (DRASIC) (Mammalian neuronal DEG/ENaC channels have several names. The names of the three channels, listed in the order of their publication are: (1) BNC1, MDEG, BNaC1, ASIC2, and the splice variant MDEG2; (2) BNaC2, ASICα, ASIC1, and the splice variant ASICβ; and (3) DRASIC and ASIC3.)(Babinski, et al. (1999); de Weille, et al. (1998); Waldmann, et al. (1997)). BNC1, MDEG2, ASICα, and DRASIC are expressed in the central nervous system (Chen, et al. (1998); Lingueglia, et al. (1997); Olson, T. H., Riedl, M. S., Vulchanova, L., Ortiz-Gonzalez, X. R., and Elde, R. (1998). An acid sensing ion channel (ASIC) localizes to small primary afferent neurons in rats. Neuron 9, 1109–1113; Waldmann, et al. (1997)). ASICα, ASICβ, DRASIC and MDEG2 are expressed in sensory neurons of the dorsal root ganglia (DRG) (Babinski, et al. (1999); Chen, et al. (1998); Olson, et al. (1998); Waldmann, et al. (1997)).

For the foregoing reasons, there is a need for determination and characterization of the roles of FMRFamide and FMRFamide-related peptides in potentiation of DEG/ENaC channels, especially the acid-sensing ion channels.

SUMMARY OF THE INVENTION

The present invention identifies a family of proteins that potentiates the effects of a group of acid-sensing ion channels (DEG/ENaC) which are responsible for pain associated with pain from ischemia and inflammation and certain other physiological effects.

An object of the invention is an assay for screening compositions which effect the acid-sensing ion channels.

Another object of the invention is an assay for screening analgesics.

A further object of the invention is a kit which can be used for performing the assay.

Yet another object of the invention is drug compositions identified by the screening assay.

These and other objects, features, and advantages will become apparent after review of the following description and claims of the invention.

FMRFamide and FMRFamide-like peptides modulate acid-activated currents. The present invention provides an assay for screening compositions to identify those which are agonists, antagonists, or modulators of acid-sensing channels of the DEG/ENaC family. This assay can be especially useful for determining analgesics. The assay comprises administering the composition to be screened to cells expressing acid-gated channels and then determining whether the composition inhibits, enhances, or has no effect on the channels when acid is introduced. The determination can be performed by analyzing whether a current is sustained by the cells in the presence of the composition and the acid. This current can be compared to that sustained by the FMRFamide and related peptides. This assay can also be provided in kit form.

BRIEF DESCRIPTION OF THE DRAWINGS

FIG. 1. Proton-gated currents in rat DRG neurons are modulated by FMRFamide.

(A) Trace of proton-gated whole-cell current; FMRFamide (100 μM) and pH 5 solution were present in bath during time indicated by bars. Unless otherwise indicated, pH was 7.4. N=8.

(B) Naloxone (100 μM) was present during time indicated by bar. N=3.

(C) Morphine (50 μM) and FMRFamide (50 μM) were added as indicated. N=3.

(D) Neuropeptide FF (NPFF) (50 μM) and FMRFamide (50 μM) were present at times indicated by bar. N=5.

FIG. 2. Effect of FMRFamide on $H^+$-gated DEG/ENaC family members. Data are representative traces from Xenopus oocytes expressing ASICα (A), ASICβ (B), DRASIC (C), or BNC1 (D), from water-injected oocyte (E), and from HEK-293T cells expressing ASICα (F). Unless otherwise indicated, extracellular pH was 7.4. FMRFamide (50 or 100 μM) and pH 5 solution were present in extracellular solution during time indicated by bars. Experiments were repeated at least 7 times.

FIG. 4. Effect of order of FMRFamide and acid addition. Data are whole-cell currents from Xenopus oocytes expressing ASICα (A, C) (n=5 each), HEK-293T cells expressing ASICα (B) (n=8). Roman numerals indicate specific interventions referred to in text. pH was 7.4 unless otherwise indicated. FMRFamide (50 or 100 μM), and pH 5 solution were present in bath during times indicated by bars. In panel D, cell was continuously perfused with solution, at pH 7.4 or pH 5, for 80 sec during time indicated by box.

FIG. 5. Properties of FMRFamide-modulated ASICα current. Data are from Xenopus oocytes (A, B, D-F) or HEK-293T cells (C) expressing ASICα.

(A) Effect of FMRFamide concentration on potentiation of $H^+$-dependent sustained current. Oocytes were exposed to indicated concentrations of FMRFamide prior to and during current activation with pH 5 solution. Measurements were normalized to the value of sustained current obtained with 500 μM FMRFamide. Data are mean±SEM; n=6–7.

(B) Effect of amiloride on FMRFamide and acid-induced sustained current. Amiloride (1 mM), FMRFamide (50 μM), and pH 5 are indicated by bars. N=5.

(C) Amiloride (100 μM), FMRFamide (100 μM), and pH 5 are indicated by bars. N=3.

(D) pH-sensitivity of ASICα current with addition of FMRFamide. FMRFamide (50 μM) was added prior to acidification. Values were normalized to current obtained at pH 3 for the transient and the FMRFamide-modulated sustained current. Data are mean±SEM; n=7.

(E, F) Current-voltage relationships of ASICα current measured at pH 5 in the presence and absence of FMRFamide (50 μM). Extracellular bath solution containing either 116 mM $Na^+$, $K^+$, or $Li^+$, as indicated. Membrane voltage was stepped from a holding voltage of −60 mV to voltages of −80, −10, or +60 mV immediately before acidification. Currents from each cell were normalized to current obtained in the same cell at −80 mV in the $Na^+$ solution (100%) (E) or the sustained currents (F). Data are mean±SEM; n=8 cells for $Na^+$ solution and 4 cells for $K^+$ and $Li^+$ solutions.

FIG. 7. Effect of FMRFamide and FRRFamide on $H^+$-gated DEG/ENaC family members expressed in Xenopus oocytes. (A, B) ASICα and ASICβ. FMRFamide (50 μM), FRRFamide (50 μM), and pH 5 solution were present in extracellular solution during time indicated by bars. N= at least 8. (C) DRASIC. FMRFamide (100 μM), FRRFamide (100 μM), and pH 4 solution were present as indicated by bars. N=6.

DETAILED DESCRIPTION OF THE INVENTION

The current invention utilizes the finding that FMRFamide and FMRFamide-like peptides directly modulate the acid-sensing ion channels. This finding can be used to determine compositions that will be useful in altering the response of these channels. Since these peptides and channels appear to have a role in nociception, compositions can be screened for inhibition of acid-sensing ion channels and antagonism of FMRFamide-related peptides to find new analgesics. Also, since FMRFamide-related peptides can induce blood pressure effects, behavior effects, and insulin and somatostatin secretion effects, screening of compositions with inhibiting or enhancing effects of acid-sensing ion channels is expected to provide useful drugs which can regulate these physiological responses as well.

FMRFamide-related neuropeptides potentiate currents from acid-sensing DEG/ENaC channels. The localization of acid-sensing ion channels and FMRFamide-like peptides suggest the two may interact in vivo. Both DRASIC and neuropeptide FF are found in the DRG (Allard, M., Rousselot, P., Lombard, M. C., and Theodosis, D. T. (1999).

Evidence for neuropeptide FF (FLFQRFamide) in rat dorsal root ganglia. Peptides 20, 327–333; Chen, et al. (1998); Waldmann, et al. (1997)). They are also both localized in the spinal cord and brain (Chen, et al. (1998); Majane, E. A., Panula, P., and Yang, H. Y. (1989). Rat brain regional distribution and spinal cord neuronal pathway of FLFQPQRF-NH$_2$, a mammalian FMRF-NH$_2$-like peptide. Brain Res 484, 1–12; Majane, E. A., and Yang, H. Y. (1987). Distribution and characterization of two putative endogenous opiod antagonist peptides in bovine brain. Peptides 8, 657–662). Moreover, FMRFamide immunoreactivity that does not appear to be neuropeptide FF is found in DRG and the brain (Ferrarese, C., Iadarola, M. J., Yang, H.-Y. T., and Costa, E. (1986). Peripheral and central origin of Phe-Met-Arg-Phe-amide immunoreactivity in rat spinal cord. Regulatory Peptides 13, 245–252; Majane and Yang (1987); Vilim, et al. (1999)). Surprisingly, FMRFamide was more potent than neuropeptide FF in activating ASIC and DRG currents.

The discovery that FMRFamide activated the molluscan FaNaCh showed that a peptide neurotransmitter could directly gate an ion channel (Lingueglia, et al. (1995)). Several studies suggested that FMRFamide-like peptides can activate multiple types of receptors in mammals. These may include an opiod receptor, a G protein coupled receptor that activates second messenger pathways, and other receptors that so far have remained unidentified (Gherardi, N., and Zajac, J. M. (1997). Neuropeptide FF receptors of mouse olfactory bulb: binding properties and stimulation of adenylate cyclase activity. Peptides 18, 577–583; Kavaliers (1987); Nishimura, et al. (2000); Payza, K., and Yang, H. Y. (1993). Modulation of neuropeptide FF receptors by guanine nucleotides and cations in membranes of rat brain and spinal cord. J Neurochem 60, 1894–1899; Raffa and Connelly (1992)). The data of the Examples below are the first indicating that mammalian members of the DEG/ENaC channel family also respond to FMRFamide-like peptides.

Acidosis is associated with inflammation and ischemia and activates cation channels in sensory neurons. Inflammation also induces expression of FMRFamide-like neuropeptides which modulate pain. Neuropeptide FF and FMRFamide generate no current on their own, but potentiate H$^+$-gated currents from cultured sensory neurons and heterologously expressed ASIC and DRASIC channels. The neuropeptides slow inactivation and induce sustained currents during acidification. The effects are specific; different channels show distinct responses to the various peptides. The results suggest that acid-sensing ion channels may integrate multiple extracellular signals to modify sensory perception. Evidence that FMRFamide directly modulates acid-sensing channel function includes the following:

(a) The effect of FMRFamide was not mimicked by morphine or blocked by naloxone.

(b) FMRFamide had the same effect on ASICα expressed in widely divergent cell types, *Xenopus oocytes* and a human cell line. If the effect of FMRFamide were indirect, both cell types would have to express similar endogenous receptors coupled to similar second messenger systems.

(c) In cells expressing the various individual acid-gated channels, FMRFamide, FRRFamide, and neuropeptide FF generated currents that were not only quantitatively different, but, more importantly, were also qualitatively different. If these neuropeptides had different affinities for an unidentified endogenous receptor coupled to a second messenger, then only quantitative differences would be expected. Moreover, such a scenario would predict that the quantitative effects would be similar for the different channels. This was not the case.

(d) Application of FMRFamide altered ASICα function in excised, outside-out patches of membrane in which the cytosol is not present.

The current data show that the FMRFamide or FMRFamide-like peptides interact with the ASIC and DRASIC channels which are evolutionarily related to the molluscan FaNaCh. However, FMRFamide did not open these mammalian channels on its own, rather it modulated the response to another agonist, protons. These findings show that a FMRFamide-binding site has been at least partly conserved in these DEG/ENaC channels, but that changes in structure have altered the consequences of the interaction.

The alternatively spliced isoforms, ASICα and ASICβ, are identical over most of their length; however, the amino acid sequence from their N-termini, through M1, and for a short distance (approximately 100 amino acids) into the extracellular domain is not the same. Differences in the response of ASICα and ASICβ to FMRFamide and FRRFamide suggest that the more N-terminal portions of ASIC contribute to the interaction with FMRFamide. That, plus the distinct interactions of FMRFamide and neuropeptide FF with FaNaCh and DRASIC and the lack of a response with BNC1, provide a strategy and the reagents to investigate where and how these channels interact with FMRFamide and related peptides.

The current data may also have implications for DEG/ENaC function in the brain. For example, intracerebroventricular injection of FMRFamide-related peptides induces a variety of physiologic responses (Kavaliers and Hirst (1985); Kavaliers (1987); Mues, G., Fuchs, I., Wei, E. T., Weber, E., Evans, C. J., Barchas, J. D., and Chang, J.-K. (1982). Blood pressure elevation in rats by peripheral administration of Tyr-Gly-Gly-Phe-Met-Arg-Phe and the invertebrate neuropeptide, PheMet-Arg-Phe-NH2. Life Sciences 31, 2555–2561; Muthal, A. V., Mandhane, S. N., and Chopde, C. T. (1997). Central administration of FMRFamide produces antipsychotic-like effects in rodents. Neuropeptides 31, 319–322; Raffa and Connelly (1992); Raffa, et al. (1986); Roumy and Zajac (1998); Sorenson, R. L., Sasek, C. A., and Elde, R. P. (1984). Phe-Met-Arg-Phe-amide (FMRF-NH2) inhibits insulin and somatostatin secretion and anti-FMRF-NH2 sera detects pancreatic polypeptide cells in the rat islet. Peptides 5, 777–782; Tang, et al. (1984); Thiemermann, et al. (1991); Yang, et al. (1985)). Recently, it was demonstrated that an amiloride analog inhibits FMRFamide-induced regulation of the brain renin-angiotensin system and hypertension (Nishimura, et al. (2000)). This suggests that these channels are a target of FMRFamide in the brain.

Proton-gated DEG/ENaC channels may function to integrate the response to acid and neuropeptides in the nervous system. Interestingly, another channel thought to be involved in nociception, the capsaicin receptor, also integrates multiple stimuli, heat and acidosis (Caterina, M. J., Schumacher, M. A., Tominaga, M., Rosen, T. A., Levine, J. D., and Julius, D. (1997). The capsaicin receptor: a heat-activated ion channel in the pain pathway. Nature 389, 816–824; Tominaga, M., Caterina, M. J., Malmberg, A. B., Rosen, T. A., Gilbert, H., Skinner, K., Raumann, B. E., Basbaum, A. I., and Julius, D. (1998). The cloned capsaicin receptor integrates multiple pain-producing stimuli. Neuron 21, 531–543). Thus in neurons, H$^+$-gated currents could vary depending upon the type and combinations of DEG/ENaC subunits expressed and on the presence of different FMRFamide-like neuropeptides. The diversity of channel subunits and neuropeptides offer rich opportunities for interactions and new targets for pharmacotherapy.

Protocols for screening new drugs, kits which utilize the protocols, and drugs selected by the screening protocols envisioned from the current findings may take into account the further characterization information below.

It has been suggested that tissue ischemia and inflammation cause pain by stimulating $H^+$-gated cation currents (Reeh and Steen (1996)). The sustained component of those currents is thought to be particularly important (Bevan and Yeats (1991); Lingueglia, et al. (1997)). Thus, the ability of neuropeptide FF and FMRFamide to induce sustained currents suggests these peptides and the acid-gated channels play a role in nociception. Interestingly, these peptides have been previously linked to pain perception in the spinal cord and brain. For example, chronic inflammation induces neuropeptide FF expression in the spinal cord (Kontinen, et al. (1997); Vilim, et al. (1999)). FMRFamide-related peptides may also contribute to opiate tolerance, in which increasing amounts of opiates are required to achieve the same analgesic effect (Raffa (1988); Roumy and Zajac (1998)). This may in part be explained by opiate-induced secretion of FMRFamide-related peptides from spinal cord neurons possibly inducing hypersensitivity of the nociceptive neurons (Tang, et al. (1984)).

The data indicates that the largest sustained currents in cells expressing ASICα required FMRFamide addition before lowering of extracellular pH but could maintain the sustained current if the amide was removed while the pH was being lowered. This suggests that the effect of FMRFamide is only reversible at pH 7.4.

Figure 4A:
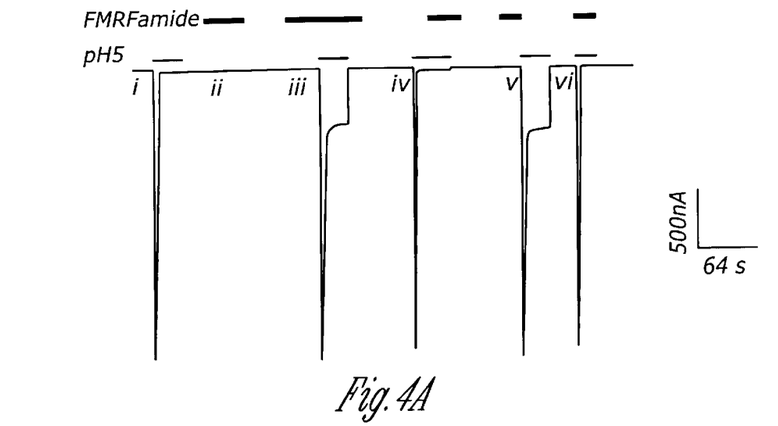
Figure 4B:
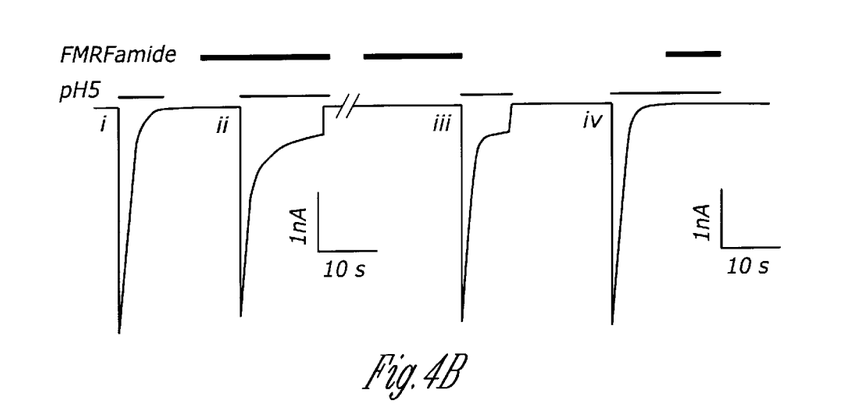
Figure 4C:
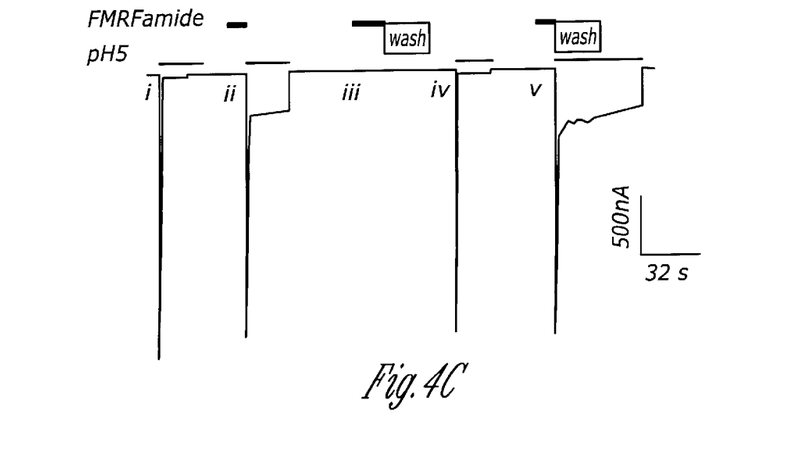

It is intriguing that FMRFamide should be applied before acid considering that ASIC and FMRFamide interact directly. The results suggest the following model. At pH 7.4, FMRFamide binds and is free to dissociate. However, when FMRFamide is bound at pH 7.4 and then pH is lowered, FMRFamide becomes trapped in the binding site. When the binding site is unoccupied, the channel inactivates rapidly, even in the continued presence of acid. However, when the binding site contains FMRFamide, channel inactivation is slowed and/or partially prevented. This scenario explains two other observations. The limited ability of the peptide to alter current when applied after acidification could be explained by a conformational change at a low pH that occludes or hides the FMRFamide binding site (FIGS. 4A, 4B). Trapping of FMRFamide within an occluded binding site at low pH would explain the continued generation of sustained currents, even after the peptide was removed from the bath (FIG. 4D). This interpretation is consistent with the earlier observation that acid pH causes a conformational change in the related BNC1 channel which altered the extracellular solvent accessibility of a specific residue (Adams, C. M., Snyder, P. M., Price, M. P., and Welsh, M. J. (1998). Protons activate brain $Na^+$ channel 1 by inducing a conformational change that exposes a residue associated with neurodegeneration. J Biol Chem 273, 30204–30207).

The data from the Examples also indicates the levels of FMRFamide which induce changes in level of sustained currents. A level of approximately 1 μM induced detectable sustained currents in cells expressing ASICα while maximal sustained currents were achieved at approximately 250 μM. Half-maximal sustained currents were achieved at approximately 33 μM. The sustained current showed different cation selectivity and pH response. FMRFamide-induced sustained currents showed sensitivity to a broader range of pH compared to transient currents.

The data indicates that for the ASICα tested FMRFamide, FLRFamide, and FRRFamide were the only FMRFamide-like peptides which could induce sustained currents. Therefore, the channels have neuropeptide specificity. FRRFamide showed a marked specificity difference when tested with other channels. For ASICβ, FRRFamide slowed the rate of inactivation without as large a sustained current as FMRFamide. For DRASIC, FRRFamide and FMRFamide increased the sustained current though at equivalent concentrations FRRFamide had a larger effect. The neuropeptide FF only had significant effects with DRASIC.

Though the details of the interactions of these peptides with the channels is not entirely clear, the following is suggested in addition to the above information regarding specificity. N-terminal extensions of RFamide-containing peptides did not appear to alter currents, and results indicated that the C-terminal amide is required for a response.

Additional FMRFamide-related peptides are expected to modulate acid-gated ion channels.

The foregoing and following information indicates an assay for screening compositions to identify those which are agonists, antagonists, or modulators of acid-sensing channels of the DEG/ENaC family. The assay comprises administering the composition to be screened to cells expressing acid-gated channels in the presence of acid and FMRFamide or FMRFamide-related peptides, and determining whether the composition enhances or inhibits the opening of the acid-sensing ion channels of the DEG/ENaC channel family. In addition to the ASIC and DRASIC channels, it is expected that FMRFamide or FMRFamide related peptides will potentiate acid-evoked activity of other members of the DEG/ENaC cation channel family. The determination of enhancement or inhibition can be done via electrophysical analysis. Cell current can be measured. Alternatively, any indicator assay which detects opening and/or closing of the acid-sensing ion channels can be used such as voltage-sensitive dyes or ion-sensitive dyes. An assay which caused cell death in the presence of the peptide, or agonist, would be the most definitive assay for indicating potentiation of the channels. Assays which could measure binding of FMRFamide and related peptides to the channels could identify binding of agonists, antagonists, and modulators of binding. One of ordinary skill in the art would be able to determine or develop assays which would be effective in finding compositions which effect the acid sensory ion channels. Since a sustained current is believed necessary for pain, a composition which inactivates the sustained current present when acid and FMRFamide or a related peptide activate the acid-sensing ion channels should be useful as an analgesic. The screening can be used to determine the level of composition necessary by varying the level of composition administered. The composition can be administered before or after addition of the acid and the FMRFamide or a related peptide to determine whether the composition can be used prophylactically or as a treatment to existing pain. One of ordinary skill in the art would be able to determine other variations on the assay(s).

Since the acid-sensing ion channels of the DEG/ENaC channel family and FMRFamide are implicated in other physiological responses (e.g., blood pressure, behavior, insulin and somatostatin secretion) in addition to nociception, the assay can be used to determine compositions which inhibit or enhance these responses as well. For example, agonists, antagonists, or modulators of the effect of FMRFamide-related peptides on the channels could be used to alter central neuronal function to alter behavior or treat neurologic and psychiatric diseases; alter mechanical sensitivity and treat conditions such as pain associated with touch (e.g., pain associated with Herpetic neuralgia); modulate blood pressure; alter respiration; and alter tolerance to opiods to treat opiod addiction. Additionally, these channels are potentially involved in taste, particularly sour and salt taste. Agonists, antagonists, or modulators of these channels and FMRFamide-related agents could be used to inhibit or enhance specific taste sensations. Taste sensations could be altered in response to temperature as well since the activity of these channels is enhanced by cold temperature, or generally, agonists could be used to alter the perception of cold temperature. One of ordinary skill in the art would be able to determine how to screen for the desired effects.

Compositions which bind to the channels can be identified or designed (synthesized) based on the knowledge of FMRFamide potentiation of the channels and determination of the three-dimensional structure of the channels. These compositions could act as agonists, antagonists, or modulators effecting nociception or other physiological responses.

EXAMPLES

Methods and Materials cDNA Constructs

Human ASICα was cloned from brain polyA RNA. Rat ASICβ and mouse DRASIC were cloned from DRG RNA. Human BNC1 was cloned as described in Price et al. (1996)(Price, M. P., Snyder, P. M., and Welsh, M. J. (1996). Cloning and expression of a novel human brain $Na^+$ channel. J Biol Chem 271, 7879–7882). Constructs were cloned into pMT3 for expression. The validity of the constructs was confirmed by DNA sequencing.

Cells and Expression Systems

Rat DRG neurons were cultured from Norway rats as described in Benson et al. (1999)(Benson, C. J., Eckert, S. P., and McCleskey, E. W. (1999). Acid-evoked currents in cardiac sensory neurons: A possible mediator of myocardial ischemic sensation. Circulation Research 84, 921–928). Cells were allowed to incubate overnight at room temperature and studies were done 1 to 2 days after isolation.

Expression of the cDNA constructs in *Xenopus oocytes* was accomplished by injection of plasmid DNA into the nucleus of defolliculated albino *Xenopus laevis* oocytes (Nasco, Fort Atkinson, Wis.) as described previously (Adams, C. M., Snyder, P. M., Price, M. P., and Welsh, M. J. (1998). Protons activate brain $Na^+$ channel 1 by inducing a conformational change that exposes a residue associated with neurodegeneration. J Biol Chem 273, 30204–30207). Plasmids were injected at concentrations of 100 ng/μl for most experiments. Oocytes were incubated in modified Barth's solution at 18° C. for 12–26 hr after injection. Cells injected with DRASIC were allowed to incubate for 24–48 hr before analysis.

HEK-293T cells were a gift of Dr. Mark Stinski (Univ. of Iowa). ASICα cDNA was transfected into HEK-293T cells using Transfast lipid reagents (Promega, Madison, Wis.). To identify transfected cells, pGreenlantern vector encoding green fluorescent protein (Gibco, Gaithersburg, Md.) was co-transfected with ASICα at a ratio of 1:6; transfected cells were identified using epifluorescence microscopy. Cells were studied 1–2 days after transfection.

Electrophysiological Analysis

Whole-cell currents in oocytes were measured using a two-electrode voltage-clamp as previously described (Adams, et al. (1998)). Oocytes were bathed in frog Ringers solution containing, in mM: 116 NaCl, LiCl or KCl, 0.4 $CaCl_2$, $MgCl_2$, 5 4-(2-hydroxyethyl)-1-piperazineethanesulfonic acid (HEPES), pH 7.4. Acidic solutions were buffered with 5 mM 2-(4-morpholino)-ethanesulfonic acid (MES) instead of HEPES. Membrane voltage was held at −60 mV unless otherwise noted. Most peptides and naloxone were obtained from Sigma Chemical Co. (St. Louis, Mont.) and were added to the extracellular solution. The peptide FRRFamide was synthesized by Research Genetics (Huntsville, Ala.).

During whole-cell patch-clamping of DRG neurons and transfected HEK-293T cells, the cells were bathed with an extracellular solution that contained, in mM: 128 NaCl, 5 $MgCl_2$, 1.8 $CaCl_2$, 5.4 KCl, 5.55 glucose, 20 HEPES, pH 7.5 or 5. The pipette solution contained, in mM: 120 KCl, 10 NaCl, 2 $MgCl_2$, 5 EGTA, 10 HEPES. Perfusion of cells with different solutions was done by placing the appropriate outlet in front of the cell. Data were recorded with an AXOPATCH 200 (Axon Instruments, Foster City, Calif.) and stored on a digital tape recorder. Digitization was executed by acquiring data at 400 Hz using pClamp6 (Axon Instruments, Foster City, Calif.).

Excised, outside-out patches were obtained from transfected HEK-293T cells. The bath solution contained, in mM: 140 NaCl, 2 $MgCl_2$, 1.8 $CaCl_2$, 10 HEPES at pH 7.4, or Tris(hydroxymethyl)aminomethane (Tris) or MES at pH 5. The pipette solution contained: 140 NMDG-Cl, 2 $MgCl_2$, 2 EGTA, 10 HEPES, pH 7.4.

Example 1

FMRFamide Modulates Proton-gated Current in Rat DRG Neurons

Figure 1A:
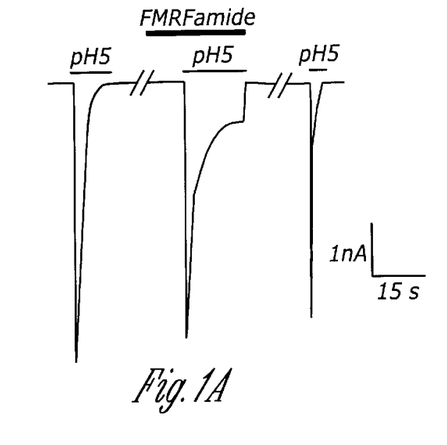
Figure 1B:
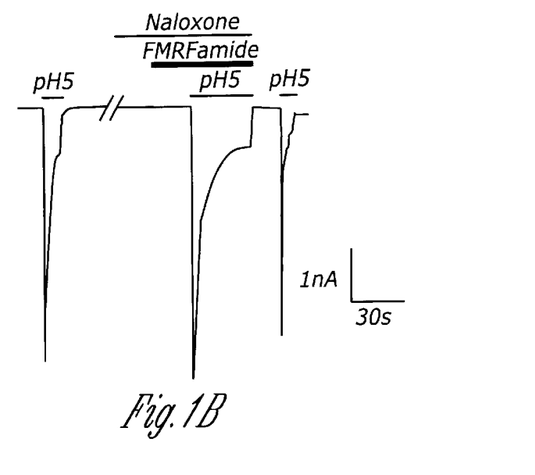
Figure 1C:
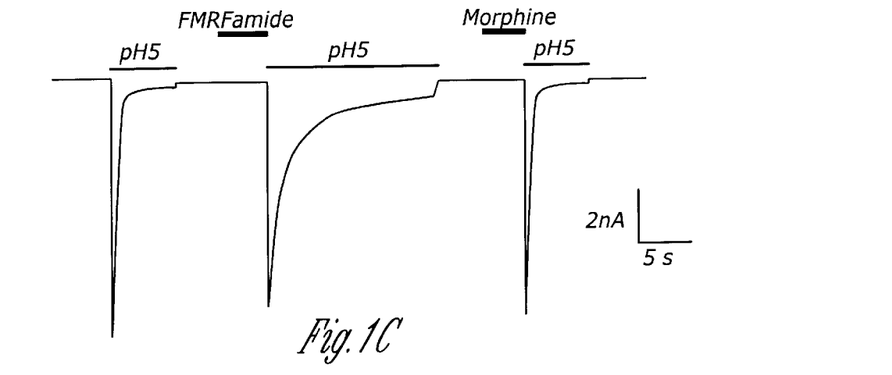
Figure 1D:
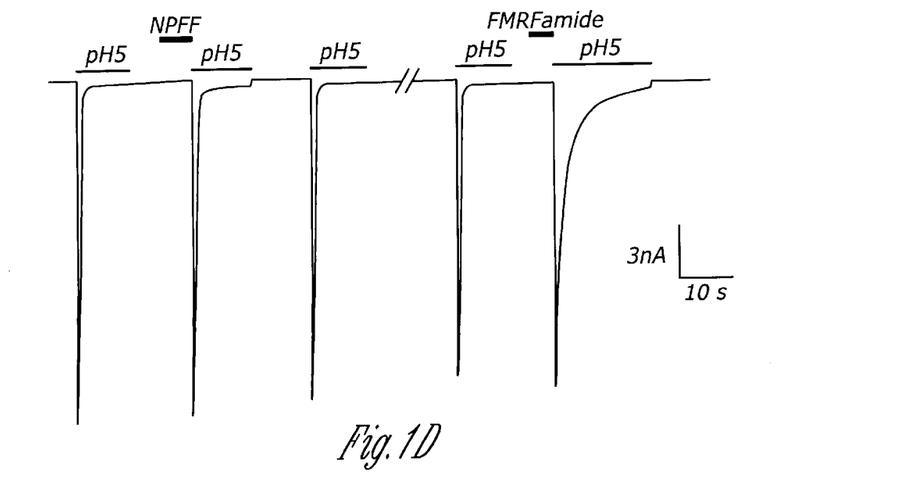

Whole-cell patch-clamp recordings were used to investigate the effect of FMRFamide on proton-gated currents in cultured rat DRG neurons. As previously reported (Akaike, N., and Ueno, S. (1994). Proton-induced current in neuronal cells. Prog Neurobiol 43, 73–83), acidification to pH 5 produced rapidly activating and inactivating currents in the sensory neurons of the DRG (FIGS. 1A–D). FMRFamide added alone generated no response from any of the neurons tested. However, after FMRFamide addition (50–100 μM), the inactivation of proton-dependent current slowed, and in many neurons, there was a sustained current in the continued presence of acid (FIGS. 1A and B). The presence of the neuropeptide immediately before acidification also altered inactivation (FIGS. 1C, 1D).

Some effects of FMRFamide are thought to be mediated through activation of opiate receptors (Raffa (1988); Roumy and Zajac (1998)). To discern whether this might account for potentiation of the proton-gated currents, the effect of naloxone, an opiate antagonist, and morphine, an opiate agonist, were used. Naloxone did not block the effect of FMRFamide (FIG. 1B), and morphine did not mimic it (FIG. 1C). These results suggested that FMRFamide was not acting through opiod receptors to alter current.

The mammalian FMRFamide-like neuropeptide FF (Phe-Leu-Phe-Gln-Pro-Gln-Arg-Phe-amide) was also tested. Neuropeptide FF modulated currents in a manner similar to FMRFamide; it generated no current on its own, but it altered inactivation of proton-gated DRF currents (FIG. 1D). The effects, however, were smaller than those generated by FMRFamide (FIG. 1D).

Example 2

Effect of FMRFamide on Acid-sensing ion Channels

Figure 2A:
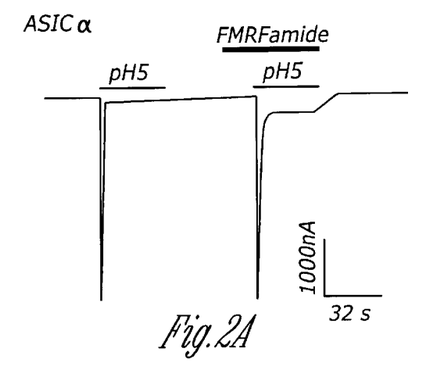
Figure 2B:
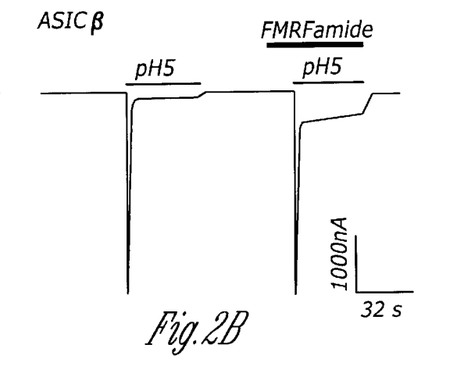
Figure 2C:
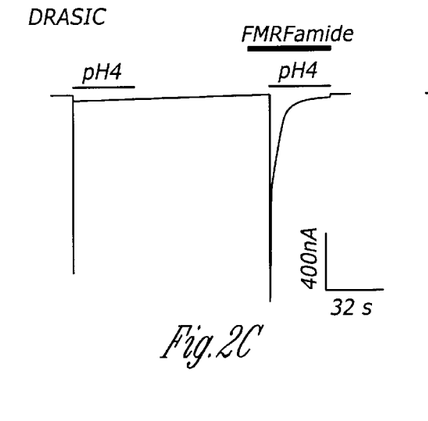
Figure 2D:
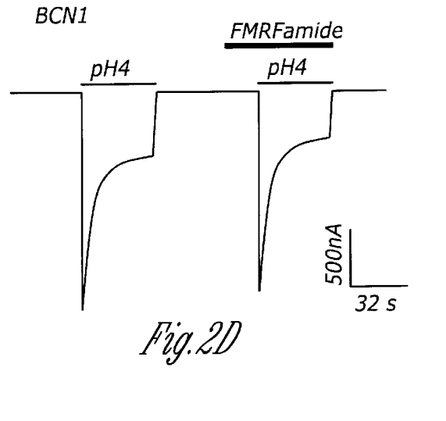
Figure 2E:
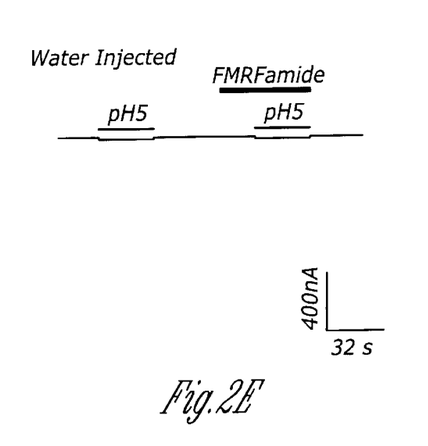

Members of the DEG/ENaC family are thought to be at least partially responsible for the acid-gated currents in the DRG. Therefore, it was reasoned that FMRFamide might have a direct effect on acid-gated DEG/ENaC channels. Mammalian acid-sensitive ion channels in *Xenopus oocytes* were expressed and the resulting currents were measured. ASICα and its alternatively spliced variant ASICβ generated rapidly inactivating currents when the extracellular pH was lowered from 7.4 to 5 (FIGS. 2A, B). In contrast to its effect on FaNaCh, FMRFamide alone had no effect on either channel. However, subsequently lowering pH in the presence of FMRFamide potentiated the current: FIGS. 2A and 2B show slowing of inactivation and the appearance of a sustained current at pH 5 in both ASICα and ASICβ. DRASIC showed a similar response in the presence of FMRFamide (FIG. 2C); following a reduction in pH, inactivation was slowed and a sustained current was more apparent. In contrast, the acid-gated currents from oocytes expressing BNC1 were not discernibly altered by FMRFamide (FIG. 2D). Neither pH nor FMRFamide in any combination produced current in control, water-injected oocytes (FIG. 2E).

Figure 2F:
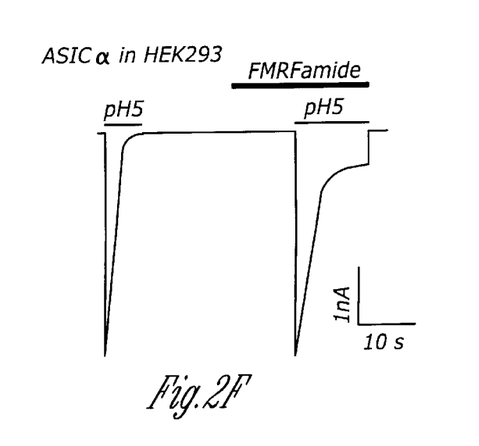

FMRFamide also altered the function of ASICα expressed in the human cell line, HEK-293T (FIG. 2F). Acidic extracellular solutions induced rapidly-inactivating whole-cell currents. In the presence of FMRFamide, inactivation slowed and a sustained current was apparent. The effect of FMRFamide on current from acid-gated channels expressed in *Xenopus oocytes* and mammalian cells mimicked that observed in DRG neurons. This similarity suggested that these DEG/ENaC channels may be responsible, at least in part, for proton-gated currents in neurons. Further studies focused on ASICα since it had been the most extensively studied, it is localized in nociceptive neurons of the DRG (Olson, et al. (1998)), and it produced a stable sustained current with FMRFamide addition.

Example 3

FRFamide Modulates ASICα Current in Outside-out Membrane Patches

Figure 3:
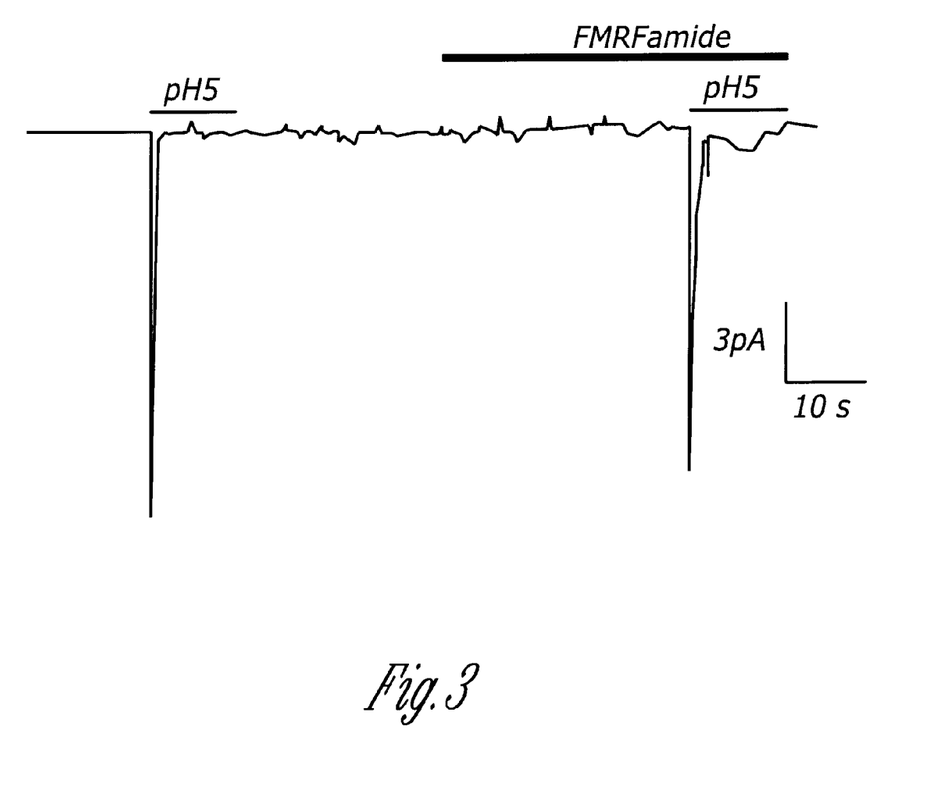
FIG. 3. FMRFamide modulates ASICα function in excised, outside-out patches. Tracing is representative of $H^+$-dependent currents recorded from HEK-293T cells transfected with ASICα. FMRFamide (100 μM) and pH 5 solution were present in extracellular solution during time indicated by bars; otherwise pH was 7.4. N=6.

To test whether FMRFamide interacts directly with the channel, ASICα was expressed in HEK293 cells and current from excised, outside-out patches was recorded. FIG. 3 shows that lowering the extracellular pH activated transient currents. In the presence of FMRFamide, inactivation was slowed substantially. These data indicated that FMRFamide directly affects ASICα.

Example 4

Sequence of Adding FMRF Amide and Acidification

In cells expressing ASICα, the presence of FMRFamide before and during acidification induced a sustained current (FIG. 4Aiii). The continued presence of FMRFamide did not prevent channel closure when pH was returned to 7.4 (FIG. 4Aiii). Thus, FMRFamide could neither activate nor sustain the current, rather it modulated acid-activated current. This stands in sharp contrast to FaNaCh which opens in response to FMRFamide alone and not acid (Lingueglia, et al. (1995)). The sequence of acid and FMRFamide application was important. The largest sustained currents required FMRFamide addition before lowering the extracellular pH; simultaneous addition of FMRFamide and acid (FIG. 4Avi) or addition of FMRFamide at pH 7.4 and then washing away the FMRFamide while simultaneously lowering pH, a sustained current still ensued (FIG. 4Av). With ASICα expressed in HEK-283T cells, the maximal sustained current also required addition of FMRFamide prior to acidification (FIG. 4Bii and 4Biii); application of FMRFamide after the pH reduction failed to induce large sustained current (FIG. 4Biv). Therefore, modulation required FMRFamide addition at pH 7.4 when the channel was closed.

FMRFamide could generate a sustained current, even when it was removed while the pH was being lowered (FIG. 4Av, FIG. 4Biii). Similar behavior was observed with acid-evoked currents in DRG cells (FIGS. 1C and 1D). The effect of removing FMRFamide from the bath solution at either pH 7.4 or pH5 was examined. FMRFamide was applied at pH 7.4, and then the bath was continuously washed for 80 sec (FIG. 4Diii). After this time, acidification generated no sustained current (FIG. 4Div). This result indicates that during the 80 sec wash, the peptide dissociated from the channel. However, when the pH was reduced while simultaneously removing FMRFamide, the sustained current persisted throughout an 80 sec pH 5 wash and beyond (FIG. 4Dv). These results suggest that the effect of FMRFamide is only reversible at pH 7.4; once the channel has been activated by acid, the effect of FMRFamide is retained until the pH is returned to 7.4

Example 5

Properties of the Current Generated by pH and FMRF Amide

Figure 5A:
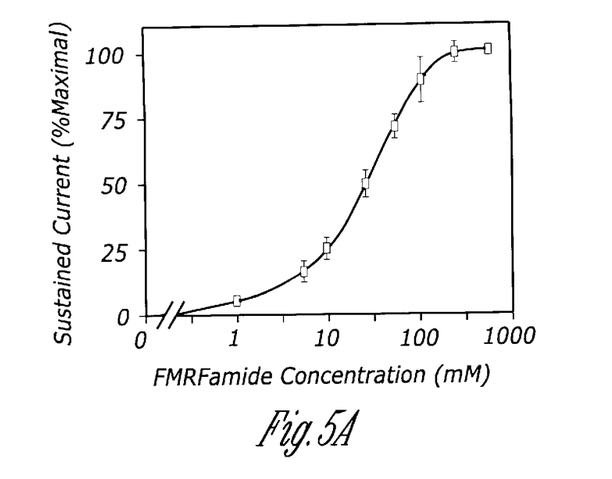

FMRFamide concentrations around 1 $\mu$M induced detectable sustained currents in cells expressing ASICα (FIG. 5A). Maximal levels of sustained current were achieved at ~250 $\mu$M FMRFamide. The FMRFamide concentration that induced half-maximal sustained currents was ~33 $\mu$M. This concentration is higher than that reported for FaNaCh (2 $\mu$M) (Lingueglia, et al. (1995)).

Figure 5B:
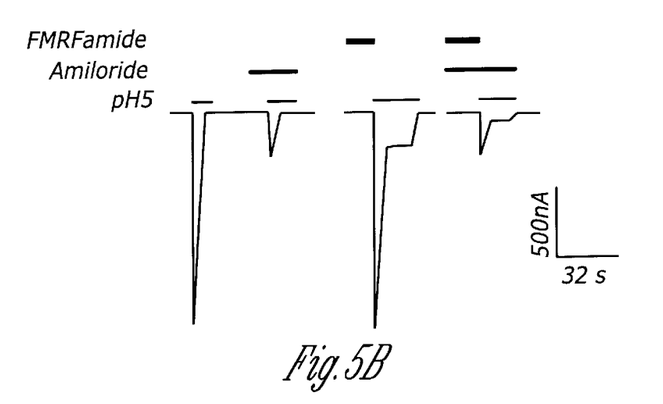
Figure 5C:
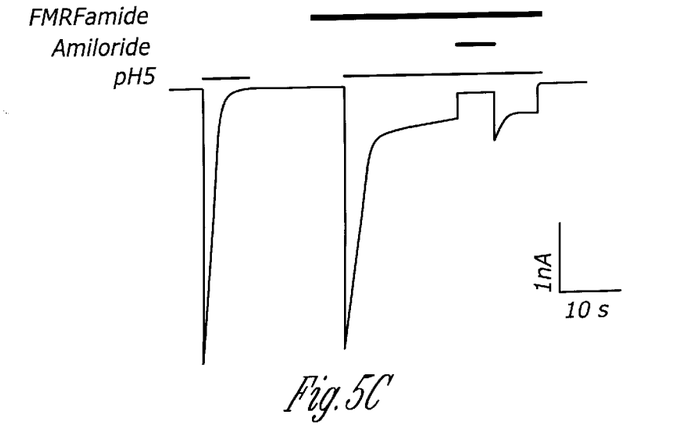
Figure 5D:
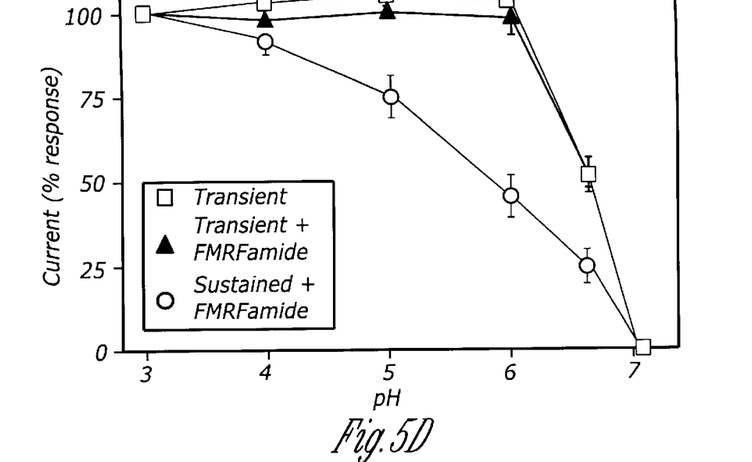

Whether FMRFamide alters the properties of ASICα transient currents and whether the FMRFamide-generated sustained current has properties different from the transient current was investigated. FIGS. 5B and 5C. show that the FMRFamide-induced sustained current was inhibited by amiloride in oocytes and HEK293 cells. FIG. 5D shows that FMRFamide did not alter the pH sensitivity of the transient current. The FMRFamide-induced sustained current, however, showed sensitivity to a broader pH range compared to the transient current. This broader range of sensitivity might allow a more graded pH response of the FMRFamide-bound channel. This may have implications for the perception of acid-evoked pain, since sustained currents are thought to play a role in pH-dependent nociception (Bevan, S., and Geppetii, J. (1994). Protons: small stimulants of capsaicin-sensitive sensory nerves. Trends Neurosci 17, 509–512).

Figure 5E:
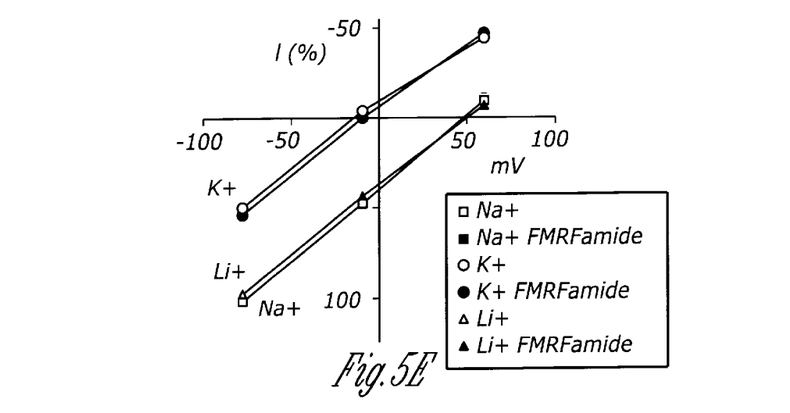
Figure 5F:
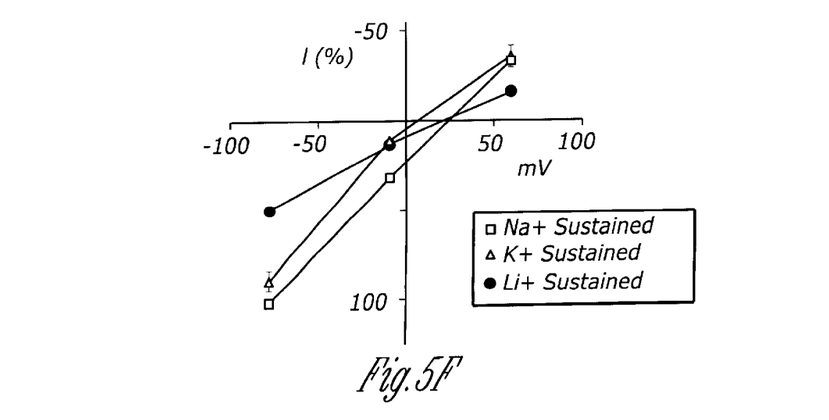

The current-voltage (I–V) relationship of the $H^+$-activated transient current of ASICα showed similar cation selectivity to what has been reported previously (Waldmann, et al. (1997)); the relative permeabilities were: $Na^+/Li^+$= 0.95±0.06, and $Na^+/K^+$=6.76±0.40. The slope conductance was similar for all the cations. The I–V relationship of the peak current was not altered in the presence of FMRFamide (FIG. 5E). The sustained current showed a somewhat different ion selectivity (FIG. 5F); the relative permeability was $Na^+/Li^+$=1.05±0.07 and $Na^+/K^+$=1.25±0.2, and the slope conductivity sequence was $Na^+ \geq Li^+ > K^+$. The sustained current did not show $Ca^{2+}$ conductance. Thus, FMRFamide did not alter the ASICα response to pH or the properties of the initial transient current. However, the sustained current showed a different cation selectivity and pH response.

Example 6

Effect of FMRFamide-like Neuropeptides on ASICα

Figure 6:
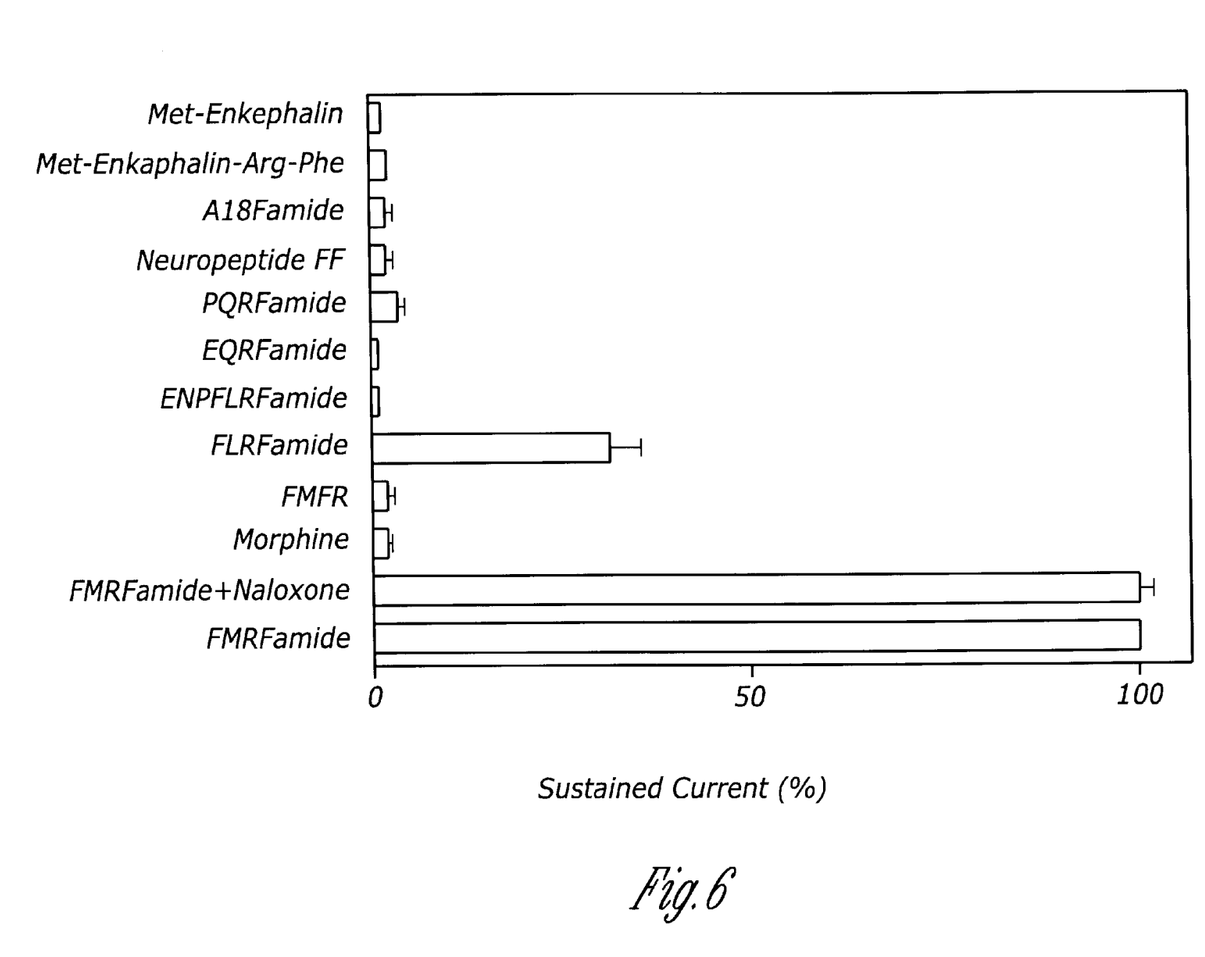
FIG. 6. Effect of FMRFamide-like peptides on ASICα current. Oocytes expressing ASICα were exposed to indicated peptides, morphine sulphate, or naloxone prior to and during acidification to pH 5. All agents were tested at 50 μM and normalized to the response to FMRFamide (50 μM) obtained in the same cell, except for A18Famide (25 μM) and naloxone (500 μM). Naloxone was applied before the addition of FMRFamide. Data are mean±SEM for 5 to 8 cells assayed for each condition.

Since FMRamide itself has not been found in mammals, whether other FMRFamide-like peptides would more potently affect ASICα was investigated. FMRFamide-like compounds were tested that have been identified in mammals including neuropeptide FF and A18Famide, which terminate with the sequence PQRFamide (Perry, S. J., Huang, E. Y. K., Cronk, D., Bagust, J., Sharma, R., Walker, R. J., Wilson, S., and Burke, J. F. (1997). A human gene encoding morphine modulating peptides related to NPFF and FMRFamide, FEBS Lett 409, 426–430; Yang, et al. (1985)) and metenkephalin-Arg-Phe (MERF), which ends with FF but lacks the amide. Neither A18Famide nor MERF altered ASICα current, and neuropeptide FF produced only minor effects on inactivation rate but no sustained current (FIG. 6 and see below). Tests were conducted of several of the many neuropeptides terminating with RFamide that have been discovered in invertebrates (Greenberg, M. J., and Price, D. A. (1992). Relationships among the FMRF-amide-like peptides. Prog Brain Res. 92, 25–37; Nelson, L. S., Kim, K., Memmott, J. E., and Li, C. (1998). FMRFamide-related gene family in the nematode, Caenorhabditis elegans. Mol Brain Res 58, 103–111; Perry, et al. (1997): Schneider, et al. (1988)). FLRFamide also induced a sustained current in ASICα, albeit less than FMRFamide (FIG. 6). N-terminal extensions of FLRFamide and other RFamide-containing peptides identified in invertebrates did not alter ASICα currents in the presence (FIG. 6) or absence of acid. FMRF-OH did not induce a response, indicating that the C-terminal amide is required. These results are similar to the neuropeptide specificity observed for FaNaCh, which has been reported to only respond to FMRFamide and FLRFamide (Cottrell, G. A. (1997). The first peptide-gated ion channel. J Exp Biol 200, 2377–2386). Morphine was tested to determine whether it could induce a sustained current and naloxone to see if it blocked FMRFamide-induced sustained current in *Xenopus oocytes*. Consistent with the results in rat DRG (FIGS. 1B and 1C), neither morphine nor naloxone altered ASICα current (FIG. 6).

Example 7

Differential Effects of FMRFamide and FRRFamide

Figure 7A:
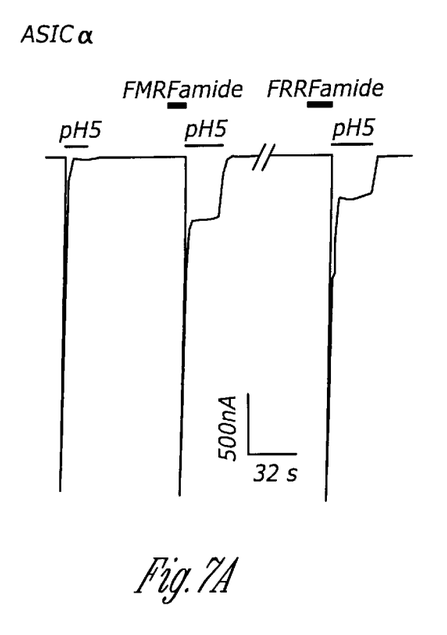
Figure 7B:
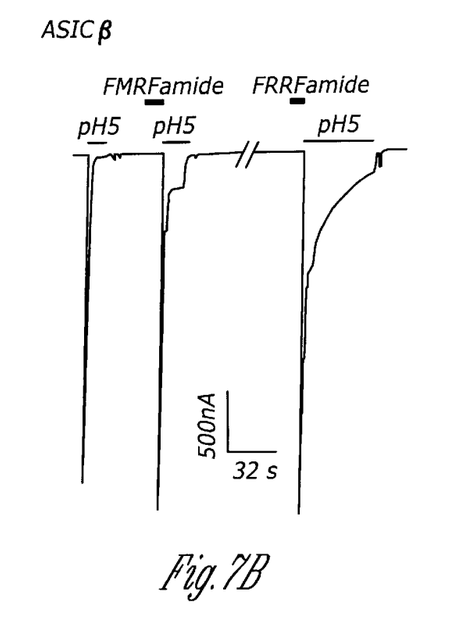
Figure 7C:
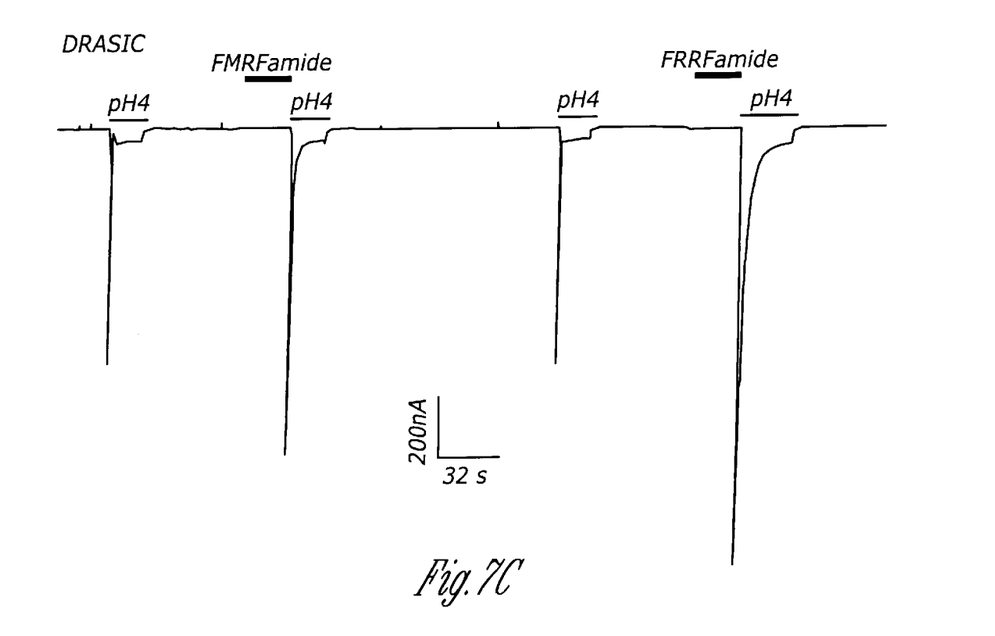

In an attempt to learn more about the peptide specificity of acid-gated channel modulation, several FXRFamide peptides were tested. One of these, FRRFamide, showed a pronounced specificity difference between acid-gated channels. With ASICα, equivalent concentrations of FRRFamide generated a sustained current similar to that produced by FMRFamide, although it was smaller in magnitude (FIG. 7A). With ASICβ, FRRFamide markedly slowed the rate of inactivation, without generating as large a sustained current as FMRFamide (FIG. 7B). With DRASIC, both FRRFamide and FMRFamide slowed inactivation of the transient current and increased the sustained current, although equivalent concentrations of FRRFamide had larger effect on transient and sustained currents (FIG. 7C).

Example 8

Neuropeptide FF Potentiates DRASIC Current

Figure 8A:
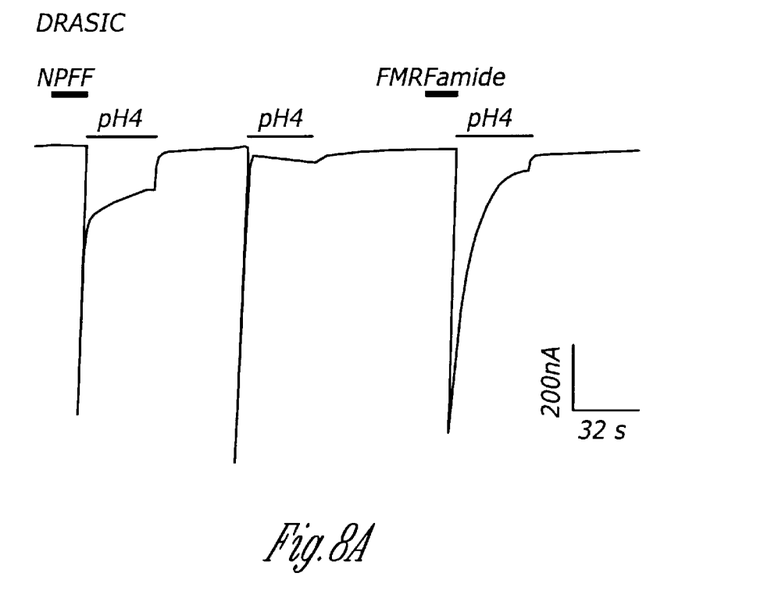
FIG. 8. Effect of neuropeptide FF on DRASIC and ASICα expressed in Xenopus oocytes. Neuropeptide FF (NPFF) (50 μM) and FMRFamide (50 μM) were present at times indicated by bars. N=5.
Figure 8B:
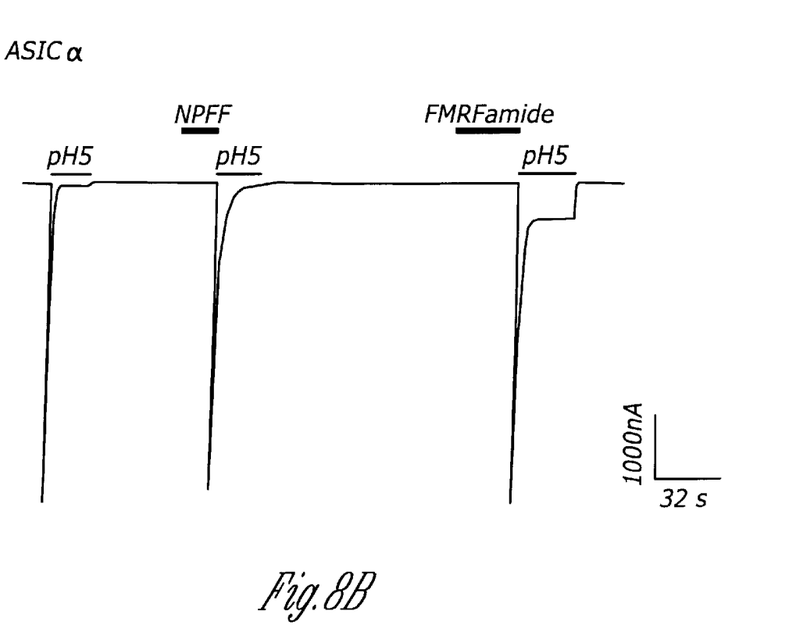

Differential modulation of the various acid-sensing ion channels by different peptides, and the finding that neuropeptide FF modulated DRG currents, suggested that this mammalian neuropeptide should be tested on all the acid-sensing channels. FIG. 8A shows that adding neuropeptide FF prior to acidification slowed the inactivation of $H^+$-gated DRASIC currents. Interestingly, the kinetics of neuropeptide FF-induced potentiation were different from those induced by FMRFamide. Neuropeptide FF had subtle effects on ASICα currents, slowing inactivation but not generating appreciable sustained current (FIG. 8B). ASICβ and BNC1 appeared unaffected by neuropeptide FF addition (data not shown).

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method for screening compositions to identify agonists, antagonists, or modulators of acid-sensing ion channels comprising administering the composition to be screened to cells expressing acid-gated channels in the presence of acid and FMRFamide or FMRFamide-related peptides, and determining whether the composition enhances or inhibits the opening of the acid-sensing ion channels of the DEG/ENaC channel family.

2. The method of claim 1 wherein the determination of opening of the acid-sensing ion channels is via electrophysical analysis.

3. The method of claim 2 wherein the electrophysical analysis looks for a sustained current in the channels.

4. The method of claim 2 wherein the electrophysical analysis looks for inactivation of a current in the channels.

5. The method of claim 1 wherein the determination of opening of the acid-sensing ion channels is via a method selected from the group consisting of voltage-sensitive dyes, ion-sensitive dyes, and cell death assays.

6. The method of claim 1 wherein the acid-gated channels are selected from the group consisting of ASIC and DRASIC channels.

7. The method of claim 1 wherein the cells are selected from the group consisting of DRG neurons, Xenopus oocytes, HEK-293T cells, cultured cell lines, and central nervous system cells.

8. A method for screening compositions to identify analgesics comprising administering the composition to be screened to cells expressing acid-gated channels, and determining whether the composition inhibits the opening of the acid-sensing ion channels of the DEG/ENaC channel family in the presence of acid and FMRFamide or related peptides.

9. The method of claim 8 wherein the determination is via electrophysical analysis.

10. The method of claim 9 wherein the electrophysical analysis looks for inhibition or inactivation of sustained current in the channels.

11. The method of claim 8 wherein the determination of opening of the acid-sensing ion channels is via a method selected from the group consisting of voltage-sensitive dyes, ion-sensitive dyes, and cell death assays.

* * * * *